(12) United States Patent
Musicco et al.

(10) Patent No.: US 11,471,137 B2
(45) Date of Patent: Oct. 18, 2022

(54) AUTOMATIC BIOPSY GUN

(71) Applicants: Pietro Musicco, Brescia (IT); Cecilia Musicco, Brescia (IT)

(72) Inventors: Pietro Musicco, Brescia (IT); Cecilia Musicco, Brescia (IT); Giorgio Ramorino, Brescia (IT)

(73) Assignees: Pietro Musicco, Brescia (IT); Cecilia Musicco, Brescia (IT)

( * ) Notice: Subject to any disclaimer, the term of this patent is extended or adjusted under 35 U.S.C. 154(b) by 539 days.

(21) Appl. No.: 15/749,041

(22) PCT Filed: Jul. 28, 2016

(86) PCT No.: PCT/IB2016/054498
§ 371 (c)(1),
(2) Date: Jan. 30, 2018

(87) PCT Pub. No.: WO2017/021826
PCT Pub. Date: Feb. 9, 2017

(65) Prior Publication Data
US 2018/0228475 A1    Aug. 16, 2018

(30) Foreign Application Priority Data

Jul. 31, 2015    (IT) .................. 102015000041055

(51) Int. Cl.
*A61B 5/00*    (2006.01)
*A61B 10/02*    (2006.01)

(52) U.S. Cl.
CPC ...... *A61B 10/0275* (2013.01); *A61B 10/0241* (2013.01); *A61B 2010/0208* (2013.01)

(58) Field of Classification Search
CPC ............ A61B 10/0275; A61B 10/0241; A61B 2010/0208
See application file for complete search history.

(56) References Cited

U.S. PATENT DOCUMENTS 4,699,154 A * 10/1987 Lindgren ........... A61B 10/0275
600/567
4,944,308 A * 7/1990 Åkerfeldt ........... A61B 10/0275
600/564

(Continued)

FOREIGN PATENT DOCUMENTS

DE    102008038413 A1    2/2010
DE    102008038414 A1    2/2010

(Continued)

*Primary Examiner* — May A Abouelela
(74) *Attorney, Agent, or Firm* — Volpe Koenig

(57) ABSTRACT

An automatic biopsy gun is described, the gun comprising a body and a needle cantileverly extending from the body. The needle comprises a stylet provided with a collecting hollow to collect a tissue sample, and a cannula in which the stylet is slidingly housed so that the collecting hollow can come out of the cannula and go back in it with a guillotine effect. The gun further comprises a pushing member to push the cannula and a pushing member to push the stylet, both being movable in the body between a forward position and a rearward position in order to slide the stylet with respect to the cannula. Elastic countering means counter the pushing members which are loaded by driving means operable by the user. Advantageously, pushing members are guided by inner guides that are inside the gun body and the guide of the cannula is closer to the needle than the guide of the stylet.

14 Claims, 10 Drawing Sheets

(56) References Cited

U.S. PATENT DOCUMENTS

| | | | |
|---|---|---|---|
| 5,036,860 A | | 8/1991 | Leigh et al. |
| 5,243,994 A | | 9/1993 | Ranalletta |
| 5,284,156 A | | 2/1994 | Schramm et al. |
| 5,570,699 A | * | 11/1996 | Kass .................. A61B 10/0275 600/567 |
| 10,675,008 B1 | * | 6/2020 | Ryu .................... A61B 10/0233 |
| 2003/0073929 A1 | | 4/2003 | Baltschun et al. |
| 2005/0124914 A1 | * | 6/2005 | Dicarlo .............. A61B 10/0275 600/567 |
| 2008/0287825 A1 | * | 11/2008 | Cooke ................ A61B 10/0275 600/562 |
| 2009/0299221 A1 | * | 12/2009 | Bacon ................ A61B 10/0275 600/567 |
| 2015/0148704 A1 | * | 5/2015 | Swick .................... A61B 10/02 600/567 |
| 2016/0324508 A1 | * | 11/2016 | Duggan ............. A61B 10/0275 |
| 2017/0035398 A1 | * | 2/2017 | Park .................... A61B 10/0283 |
| 2017/0231608 A1 | * | 8/2017 | Schässburger ..... A61B 10/0275 600/566 |
| 2018/0103939 A1 | * | 4/2018 | Van Liere .......... A61B 10/0275 |
| 2018/0168770 A1 | * | 6/2018 | Haggar ............. A61B 10/0275 |

FOREIGN PATENT DOCUMENTS

| | | |
|---|---|---|
| DE | 102011014721 A1 | 9/2012 |
| DE | 102011014722 A1 | 9/2012 |
| KR | 20130079788 A | 7/2013 |

\* cited by examiner

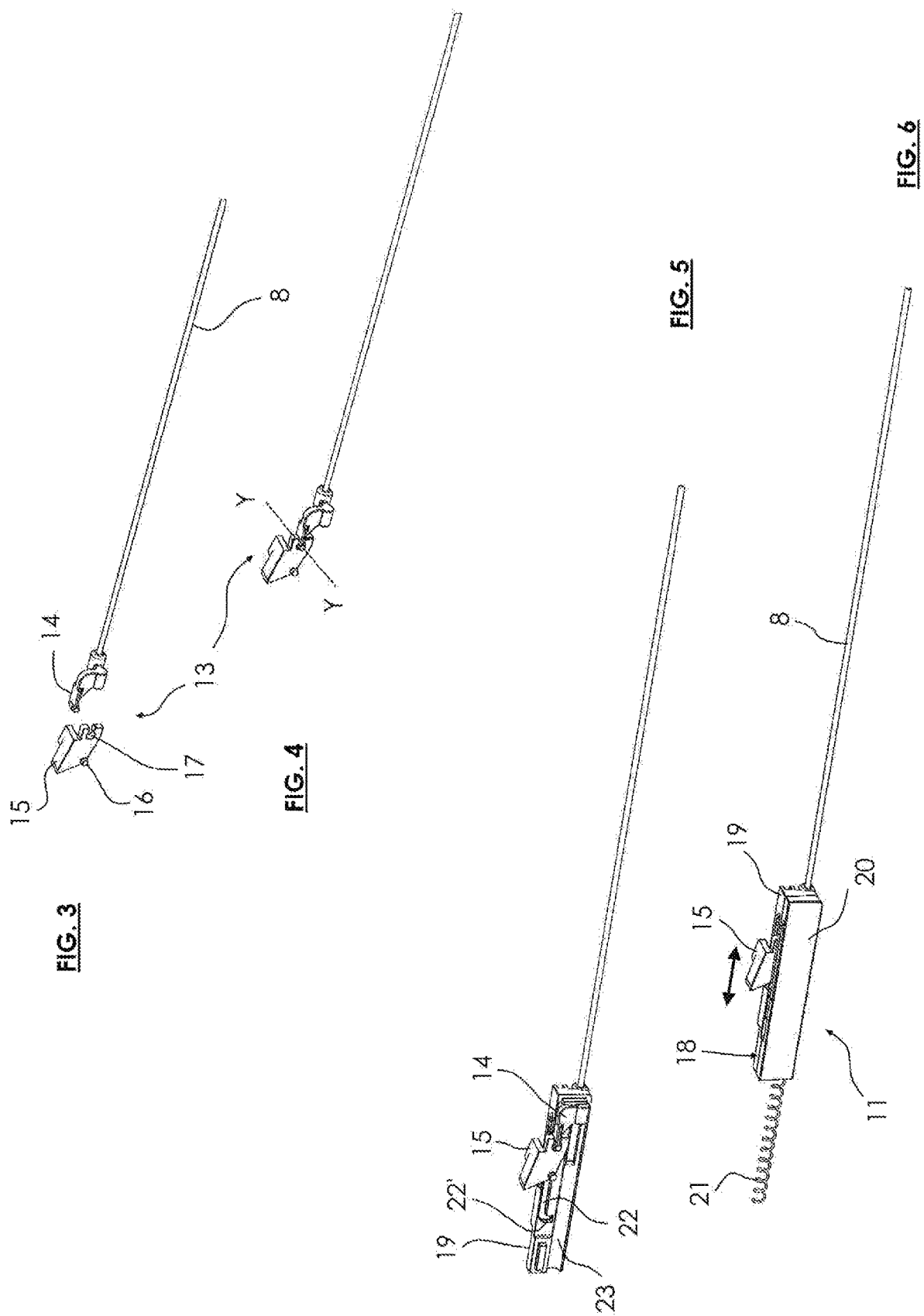

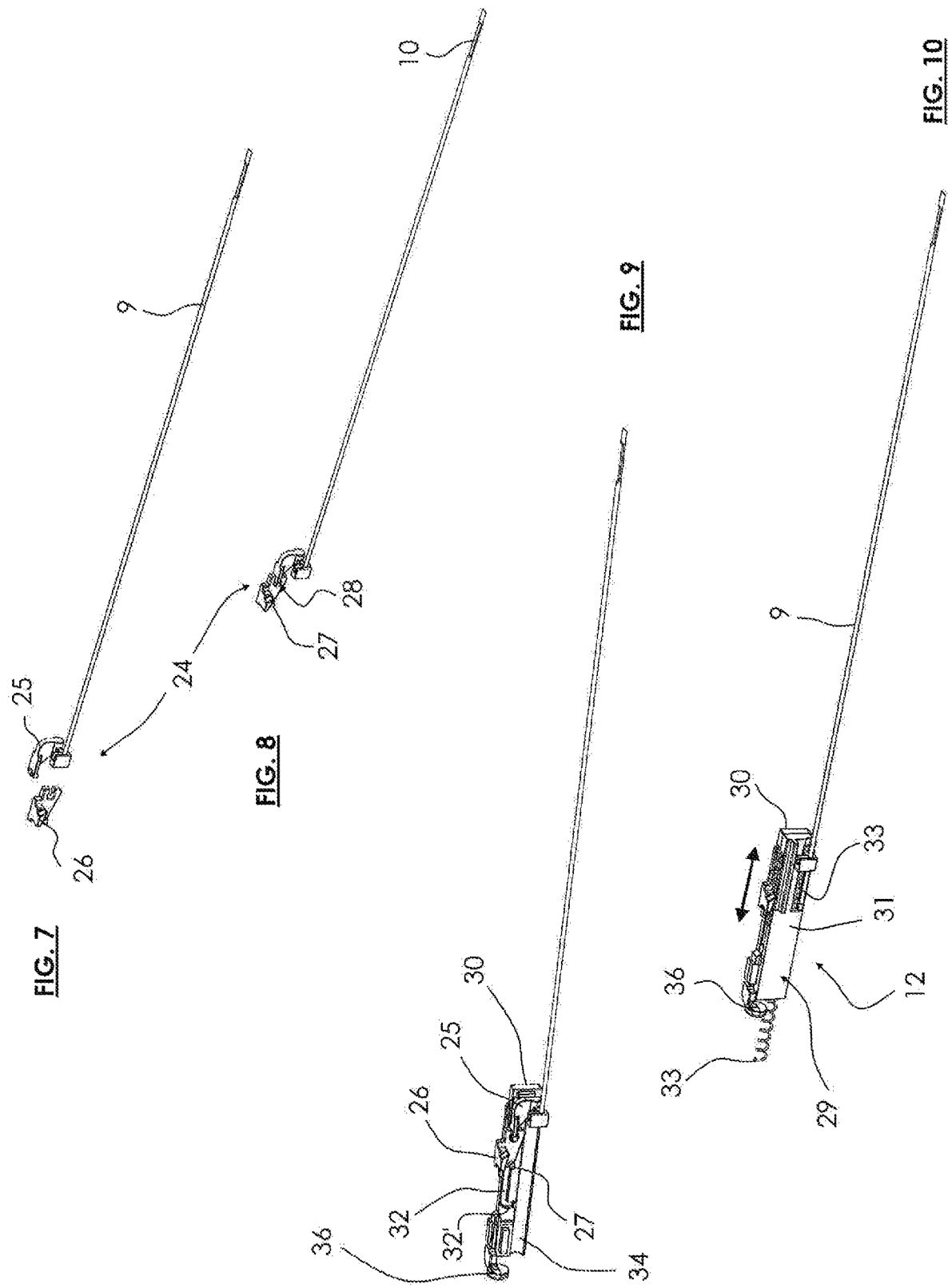

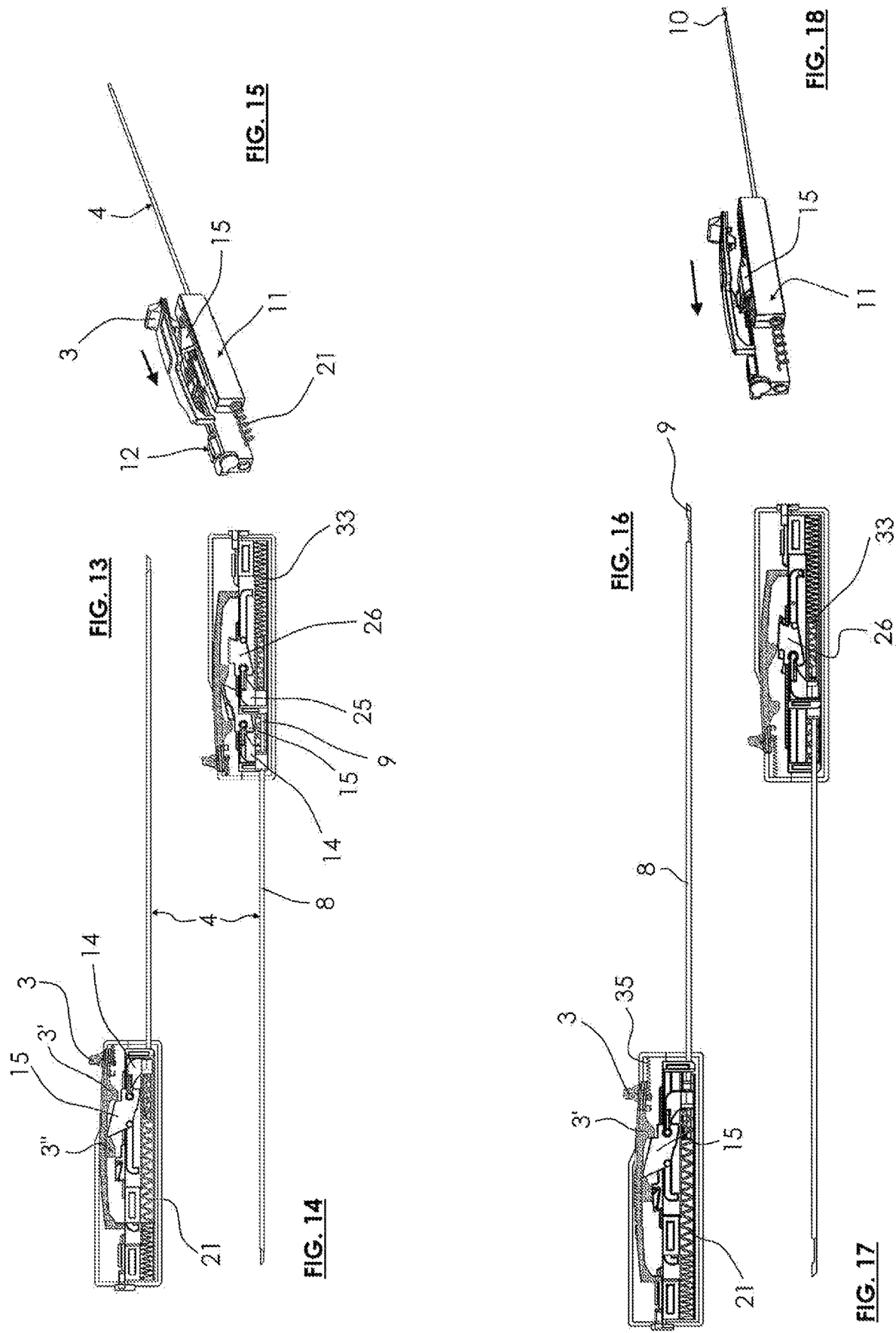

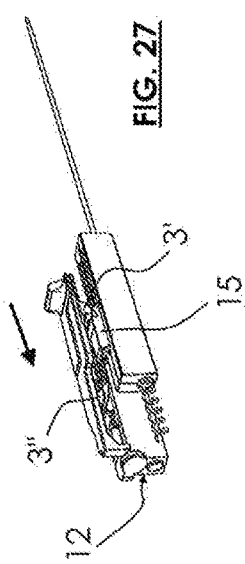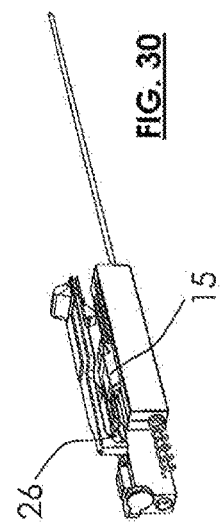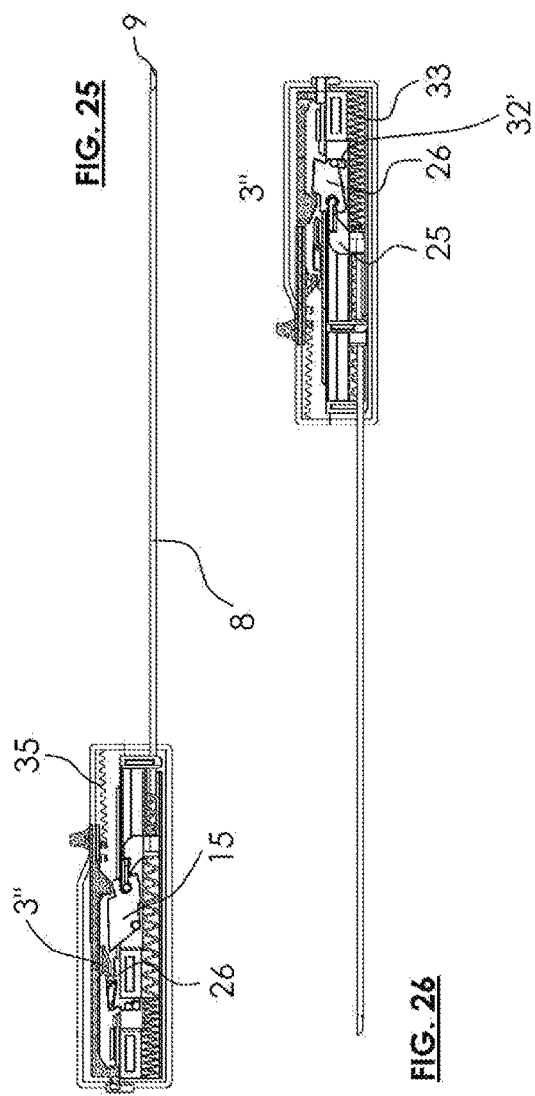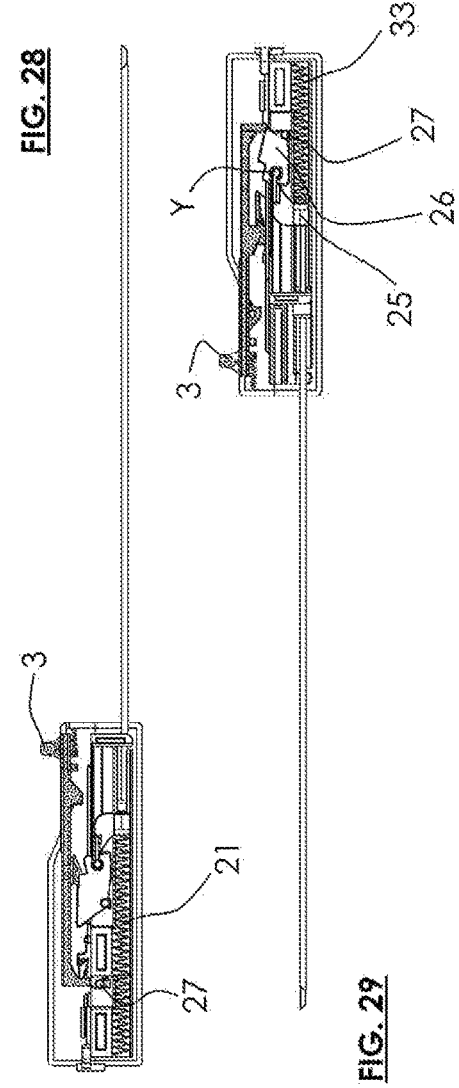

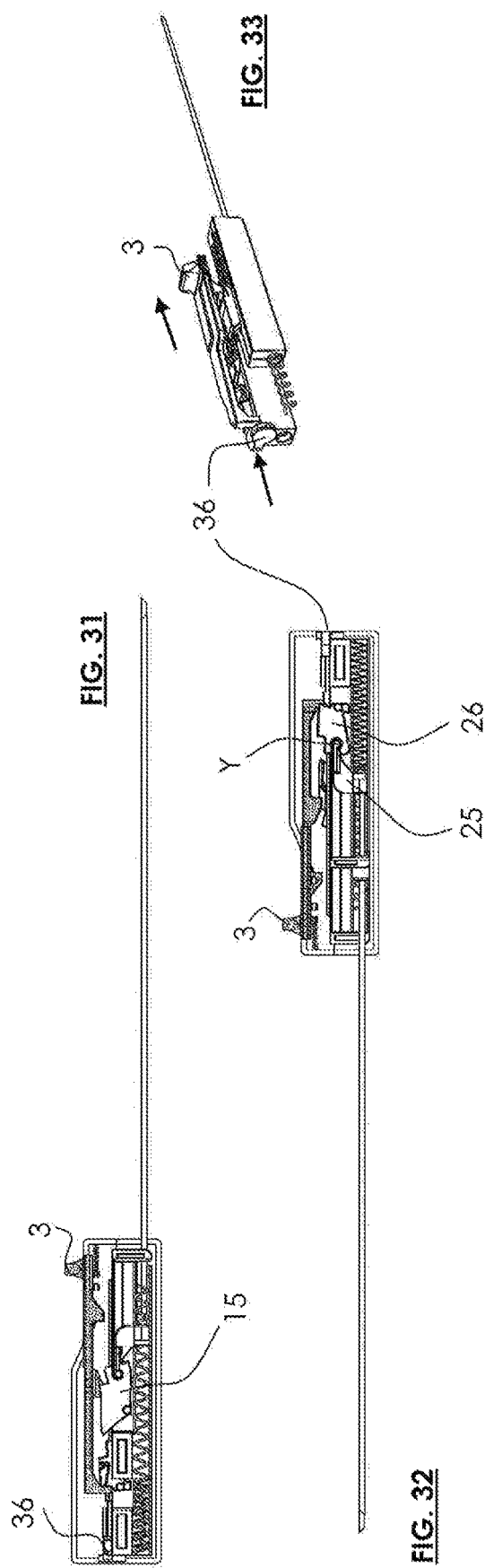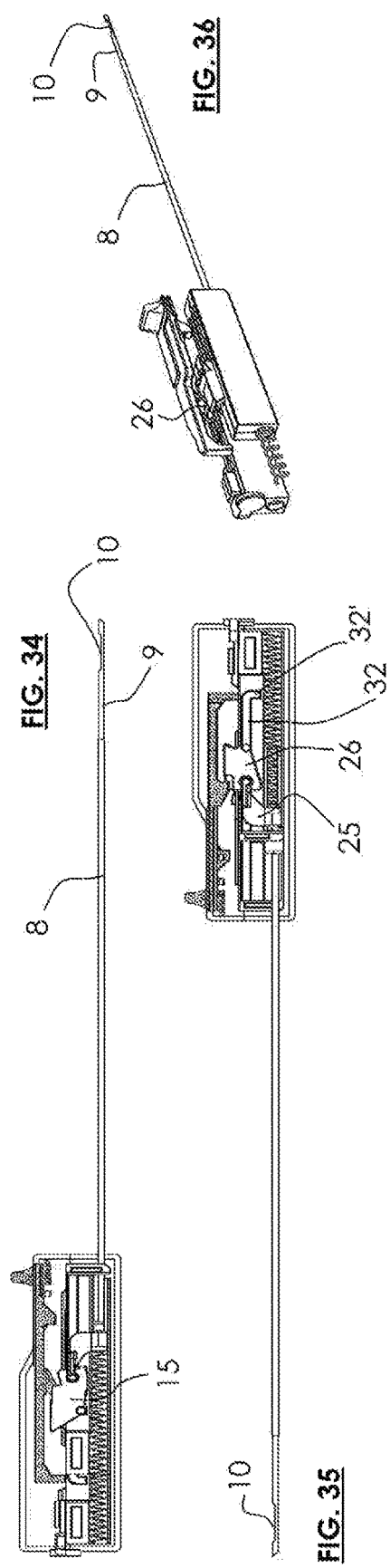

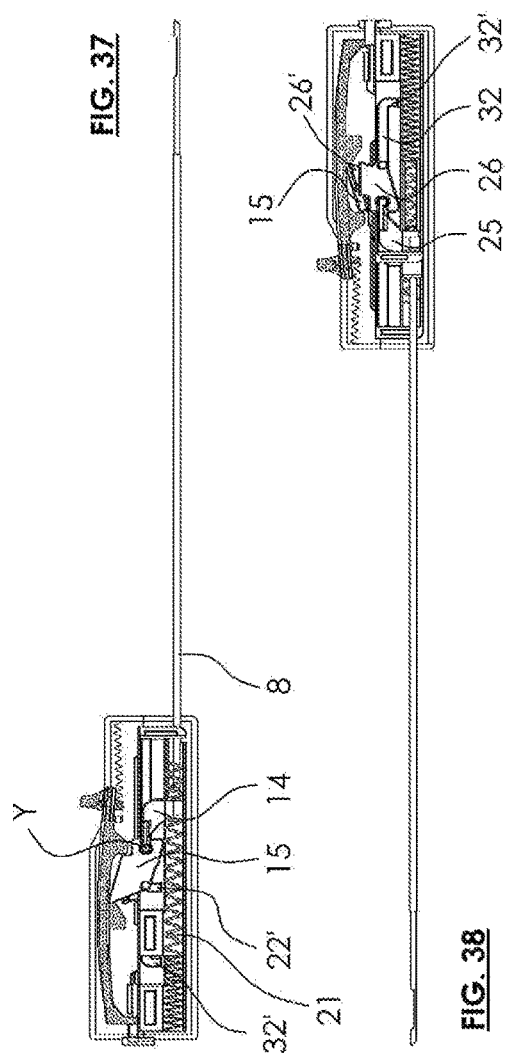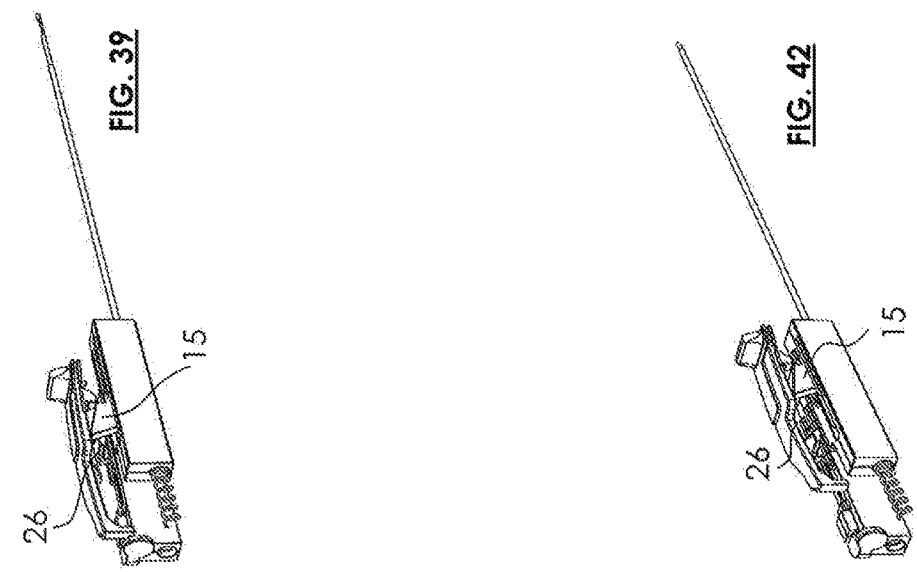

AUTOMATIC BIOPSY GUN

FIELD OF THE INVENTION

The object of the present invention is a biopsy gun, in particular an automatic gun of the type used to sample tissues from the human body.

PRIOR ART

Biopsy guns are used to sample soft tissues inside the human body, usually in order to carry out histological tests.

There are several types of gun. For example, disposable guns as well as guns able to be reused for several sampling operations and therefore providing for the use of disposable biopsy needles, are known.

The present invention relates to a disposable automatic gun using a guillotine technique for taking a soft tissue sample from the body of a patient, for example renal, prostate, breast tissue.

The following documents of the known art describe this type of guns: KR 20130079788, DE 102011014722, DE 102011014721, DE 102008038413, DE 102008038414.

Generally, disposable biopsy automatic guns comprise a box-shaped body having a disposable needle which can be removably combined therewith. The substantially parallelepiped shape of the box-shaped body allows the healthcare professional to hold it. For this reason, a first distal end corresponding to the end closest to the patient during the biopsy and farthest from the healthcare professional who holds the gun, and a proximal end corresponding to the end farthest from the patient during the biopsy and closest to the healthcare professional who holds the gun, can be identified in the box-shaped body. The disposable needle cantileverly extends from the distal end of the box-shaped body so as to be insertable in the patient's body.

The needle comprises two components:
- a cannula provided with an echogenic tip and an end constrained to a first carriage slidingly housed in the box-shaped body;
- a stylet coaxially housed in the cannula and sliding therein. The stylet has a pointed end at which a collecting hollow to collect the tissue sample is provided. The opposite end of the stylet is constrained to a second carriage slidingly housed in the box-shaped body.

The first and second carriages translate in the box-shaped body between an initial rearward position, at the proximal end of the box-shaped body, and a final forward position near the distal end of the box-shaped body. Corresponding springs apply to the carriages the pushing force required for the shifting between these two positions. The paths traveled by the two carriages are parallel to each other and parallel to the needle, which also defines the longitudinal axis of the box-shaped body.

Usually the carriages are locked in their rearward positions. A driving mechanism, named shooting mechanism, allows the healthcare professional to unlock the carriages, as explained below.

The shooting mechanism comprises a first and a second loading studs both positioned on the top or side surface of the box-shaped body of the gun. The loading studs can slide with respect to the box-shaped body, parallel to the longitudinal axis, and they act on retaining teeth of the first carriage and second carriage, respectively, or on equivalent countercheck surfaces holding the carriages in the rearward position, thereby preventing the extension of the springs.

By pressing the second stud, the healthcare professional releases both the carriages that suddenly move to the forward position under the action of the respective springs. The travel of the first carriage is completed with a minimum delay with respect to the time required by the second carriage to complete the respective forward travel. The sequential sliding of the cannula with respect to the stylet allows the above mentioned guillotine technique to be implemented.

Once the healthcare professional has inserted the needle into the patient's body and has pressed the second stud, the pointed end of the stylet comes out of the cannula and the tissue to be sampled is positioned in the collecting hollow. The subsequent sliding of the cannula over the stylet causes the separation of the tissue sample that remains trapped in the chamber defined by the collecting hollow and the cannula itself In practice, the cutting surfaces of the stylet and the cannula cooperate as a guillotine for cutting the tissue and holding it in the needle, which at this point can be pulled out of the patient's body.

The sequential movement of the stylet and the cannula is generally obtained by positioning the first carriage slightly back with respect to the second carriage. The two carriages run equal travels. Actually this feature makes the gun operation automatic. Therefore, the term automatic means that the stylet and the cannula are not separately operated by the healthcare professional, but these two components move automatically and in due time as a result of the activation of the second stud by the healthcare professionals.

The return travel of the carriages to the respective rearward positions allows the spring to be reloaded in order to be used again. The healthcare professional manually pulls the first stud and then the second stud in order to reload the springs and lead the carriages to the initial rearward position. Before completing the return travel, the healthcare professional makes sure that the stylet is exposed from the cannula just enough to collect the tissue sample taken from the patient's body.

At this point, the gun can be used for taking other samples from the same patient, and then can be replaced or provided with a new sterile needle for taken samples from other patients.

The automatic biopsy guns currently available have some drawbacks.

First of all, traditional guns have complex structure; the various components have complicated geometries and this makes them difficult to be assembled. Currently it takes about 8-10 minutes to a worker to complete assembling a gun of the just described type. Considering that the market imposes low costs for these guns, the time required to assemble should be as short as possible.

Among other things the complicated geometry of the components, with countercheck surfaces, teeth and undercuts, negatively affects production costs, since the components are mostly made of plastic and obtained by molding.

Despite the complicated geometry of the components, in traditional guns the bidirectional movement of the carriages is often poorly smooth, sometimes also in jerks.

Another drawback is that the healthcare professional must always operate both studs in order to reload the springs and return the carriages to the rearward position. This often forces to change the gripping position, that can be an uncomfortable operation.

Still another drawback that can be found in traditional automatic biopsy guns is that the springs used to push the carriages often bend, i.e. laterally warp, and this prevents all the potential energy thereof to be exploited.

U.S. Pat. No. 5,284,156 describes a biopsy gun provided with two carriages arranged in a line and movable along equal travels.

U.S. Pat. No. 5,036,860 describes a biopsy gun having a single carriage, in which the carriage is guided by cams inside the gun body. The cams are arranged as a path including straight sections and curved sections at which the carriage turns.

US 2003/0073929 describes a gun in which the carriages are loaded by telescopically inserting half of the gun body in the other half. An operating button is provided at the rear in order to release the carriages and to allow them to slide forward.

U.S. Pat. No. 5,243,994 describes a biopsy gun in which the carriages are loaded by the user by means of a cocking member (reference numeral 56 in FIG. 3) sliding on the gun body. The cocking member comprises a drive tongue 56*b* designed to engage the drive member 42. A lever arm portion 58*b* drives a ratchet wheel 66 acting on a kinematic chain for locking the sliding of the carriages.

SUMMARY OF THE INVENTION

The object of the present invention is therefore to provide an automatic biopsy gun which simply and effectively solves the drawbacks of the currently available solutions, having at the same time a simple structure, being easy to be assembled in a short time, economic and functional for the healthcare professional.

Therefore, the present invention concerns an automatic biopsy gun according to claim 1.

In particular, the gun comprises a box-shaped body, defined for example by an upper body portion and a lower body portion, and a needle cantileverly extending from the box-shaped body, in a direction defined as longitudinal.

The needle comprises in turn a stylet provided with a collecting hollow to collect a tissue sample, and a cannula. The stylet is slidingly housed in the cannula so that the collecting hollow can come out of the cannula and go back in it in order to obtain the guillotine effect.

A first pushing member is constrained to the cannula and is movable in the box-shaped body in the longitudinal direction between a forward position, at which the cannula is completely extended from the box-shaped body, and a rearward position, at which the cannula is partially inserted in the box-shaped body, i.e. partially retracted.

A second pushing member is constrained to the stylet and is movable in the box-shaped body in the longitudinal direction between a forward position, at which the stylet is completely extended from the box-shaped body, and a rearward position, at which the stylet is partially inserted in the box-shaped body.

Clearly, depending on the position taken by the first pushing member with respect to the second pushing member, either the exposure of the collecting hollow or its insertion into the cannula can be obtained.

The gun is further provided with elastic countering means to counter the first pushing member and the second pushing member. The elastic means have the function of applying a longitudinal pushing force in order to bring the cannula and the stylet in the respective advanced position during shooting.

The gun comprises driving means, operable by the user, to drive the first pushing member and the second pushing member. Driving means are designed to load the gun, i.e. to load the above described elastic means in order to be able to shoot.

Unlike known solutions, the gun advantageously comprises inner guides that are inside the box-shaped body for guiding the first and second pushing members. In other words, the pushing members are designed as follower members of the respective inner guides. The inner guide of the first pushing member and the inner guide of the second pushing member are staggered in the longitudinal direction so as to allow the exposure of the stylet tip with respect to the cannula.

The proposed solution allows the gun structure to be made remarkably easier: in fact the inner guides can be designed so as to have themselves the stops of the pushing members in the rearward position. In this way, complicated retaining systems can be avoided such as teeth and undercuts, while they are provided in known solutions in order to hold the pushing members steady against the pushing action of the elastic means.

The gun according to the present invention has a number of components less than the number of components of traditional guns, thus favoring a simplification of the assembling operations, which take 3 minutes or less to be completed.

By driving the pushing members by means of inner guides, a further advantage is achieved given by the greater smoothness and fluidity of movement of these elements with respect to known solutions. The inner guides effectively guide the respective pushing members without jamming or without generating excessive friction. In this way the energy of the elastic means can be best exploited.

Preferably, the inner guide of the first pushing member and the inner guide of the second pushing member have the same longitudinal extent, namely they allow the respective pushing members, and therefore the cannula and the stylet connected thereto, to run equal travels. The guides are staggered in the longitudinal direction by a length corresponding to the maximum possible exposure of the stylet with respect to the cannula; in other words, the stroke of the stylet with respect to cannula is obtained by positioning the guide of the first pushing member (cannula) closer to the distal end of the box-shaped body, i.e. closer to the needle, with respect to the guide of the second pushing member (stylet).

In the preferred embodiment, each inner guide mainly extends in the longitudinal direction, except at the stop corresponding to the rearward position of the respective pushing member. In fact, this stop is a deviation of the guide itself in a direction transversal to the longitudinal direction, for example a 90° corner or with an angle greater than 90°. This configuration allows the pushing members—which actually are also followers of the respective inner guide—to be temporarily locked in the stops by overcoming the action of the elastic means. As later explained, during shooting the pushing members are pushed out of the stops towards the longitudinal section of the respective guides.

Preferably, the first pushing member comprises:
a first fastening member integral with the cannula and sliding in the respective inner guide, and
a first slider hinged to the first fastening member so as to rotate with respect to the latter on an axis orthogonal to the longitudinal direction and provided with engaging portions to engage the first inner guide, so that the first slider behaves—as explained above—like a follower of the first inner guide.

Preferably, the second pushing member comprises:
a second fastening member integral with the stylet and sliding in the respective inner guide, and a second slider hinged to the second fastening member so as to rotate with respect to the latter on an axis orthogonal to the longitudinal direction and provided with engaging portions to engage the second inner guide.

The just described configuration of the pushing members allows the sliding not only of the fastening members in the sections without deviations of the inner guides, but also of the sliders both in the sections without deviations of the inner guides and in the deviations, where there is the stop and the slider remains locked even though the elastic means have been loaded. This result can be obtained thanks to the rotation of the sliders with respect to the respective fastening members. In fact, the fastening members can not rotate, because one of them is constrained to the cannula and the other one to the stylet and therefore they are not able to deviate from the longitudinal path of the inner guides; on the other hand, the sliders can follow the deviations.

Preferably, the elastic countering means of the first pushing member and the second pushing member are springs. The springs are fully extended (as far as possible inside the gun) when the respective pushing member is in the forward position and vice versa, while they are completely compressed when the respective pushing member is in the rearward position.

In the preferred embodiment of the present invention, the springs are housed in appropriate seats that prevent deformations in directions transversal to the longitudinal direction. That is, the springs can not bend or warp as in traditional solutions, but are substantially tubed, so that they are subject to deformations only in the longitudinal direction. In this way their potential energy can be best exploited.

In an embodiment, the gun comprises:
a first carriage assembly in turn provided with a first casing, and
a second carriage assembly in turn provided with a second casing.

The first pushing member and the respective countering elastic means, i.e. the first spring, are part of the first carriage assembly. The first inner guide is obtained at the inner walls of the first casing. The second pushing member and the respective countering elastic means, i.e. the second spring, are part of the second carriage. The second inner guide is obtained at the inner walls of the second casing.

Preferably, the two carriage assemblies are modular and interchangeable in the box-shaped body so as to allow them to be pre-assembled outside the box-shaped body and mounted therein, or replaced, with great easiness. This also helps to simplify the assembly and minimize the times thereof.

Preferably, the driving means consist of a loading stud mounted on the box-shaped body and sliding between a forward position and a rearward position. The loading stud is operable by the user, for example by the thumb, and comprises at least one first tooth and one second tooth both designed to engage, respectively, the first pushing member and the second pushing member, which are located in the box-shaped body.

Unlike known solutions, advantageously the gun according to the present invention comprises a single loading stud which, thanks to the two teeth just described, is designed to load both the first pushing member and the second pushing member by running two corresponding travels at different times. This feature allows the healthcare professional to effectively use the gun without having to change grip during loading.

Preferably, the loading stud is at least partially flexible for bending, or the second tooth is swinging, so to allow right the second tooth to step over the second pushing member when the first pushing member is led to the rearward position and, on the contrary, to allow engaging the second pushing member when the latter is led to the rearward position, thereby allowing the elastic means to be loaded in two times, but actually by means of a single stud. As an alternative, the loading stud is flexible and the second tooth is swinging. All this three solutions make the loading of the gun particularly convenient for the healthcare professional, even if he/she wears protective gloves.

If the second tooth is swinging, the gun may be provided with a return spring that returns the tooth in the initial lowered position, i.e. projecting from the loading stud, in order to mesh the second pushing member when the latter is led to the retracted position.

Preferably, the loading stud is designed so as to be able to further unlock the second pushing member when the latter is in the respective rearward position thereby triggering the shot.

Alternatively or additionally, the gun comprises a shooting button positioned on the box-shaped body laterally or in the back towards the user. The shooting button is adapted to unlock from the respective stop the second pushing member in order to allow it to be moved to the forward position by the elastic means.

Preferably, the second pushing member is provided with a tilted surface acting as a disengagement lever to disengage the first pushing member from the respective stop when the second pushing member is released from the rearward position to the forward position, so that also the first pushing member moves suddenly forward.

The operation of the gun according to the present invention will be now described.

Initially the gun is unloaded. The healthcare professional must load the elastic means of the first and second pushing members, and to do it he/she operates the loading stud.

A first travel run by the loading stud from the forward position to the rearward position allows both the first pushing member to be led to the respective stop in the rearward position, where it remains locked, and the respective countering means to be loaded. The stud goes back to the forward position, for example due to the returning action of an appropriate spring. The first travel run by the loading stud does not influence the second pushing member, which is by-passed without being affected by the movement. In this circumstance the cannula is retracted with respect to the stylet and the collecting hollow is exposed and accessible.

A second travel run by the loading stud from the forward position to the rearward position allows both the second pushing member to be led to the respective stop in the rearward position, where it remains locked, and the respective countering means to be loaded. The stud goes back to the almost forward position. In this circumstance, the stylet slides within the cannula and the collecting hollow is led inside the cannula.

The gun is now ready to shoot and the healthcare professional inserts the needle into the patient's body.

By pushing forward the loading stud, or by pressing the shooting button, the second pushing member is released from its stop in the rearward position; under the pushing force of the elastic means the second pushing member suddenly moves forward towards its advanced position. As a result, the stylet comes partially out of the cannula in a telescopic way, so as to expose the collecting hollow where the patient's tissue is received.

The second pushing member, before reaching the forward position at which it stops and ends its travel, intercepts the first pushing member which in the meantime was stationary in its own stop (it is recalled that the stop of the first pushing member in the rearward position is closer to the distal end of the box-shaped body with respect to the stop in the rearward position of the second pushing member). The contact between the two pushing members causes the first pushing member to disengage from the respective stop. Under the pushing force of the elastic means the first pushing member suddenly moves forward to its forward position. As a result, the cannula slides over the stylet and cover the collecting hollow in which the patient's severed tissue is held.

At this point the needle is pulled out of the patient's body and the healthcare professional pushes again the loading stud to the rearward position in order to expose the collecting hollow and take the tissue sample.

The gun is now ready to be used again.

BRIEF LIST OF FIGURES

Further characteristics and advantages of the invention will be more evident by the review of the following specification of a preferred, but not exclusive, embodiment, depicted for illustration purposes only and without limitation, with the aid of the attached drawings, in which:

FIGS. 3-6 are perspective views showing the assembling sequence of the first carriage of the gun shown in FIG. 1;

FIGS. 7-10 are perspective views showing the assembling sequence of the second carriage of the gun shown in FIG. 1;

FIGS. 13 and 14 are longitudinal sectional views of the gun shown in FIG. 1, in a first configuration;

FIG. 15 is a perspective view of inner components of the gun shown in FIG. 1 in the first configuration;

FIGS. 16 and 17 are longitudinal sectional views of the gun shown in FIG. 1, in a second configuration;

FIG. 18 is a perspective view of inner components of the gun shown in FIG. 1 in the second configuration;

FIGS. 25 and 26 are longitudinal sectional views of the gun shown in FIG. 1, in a fifth configuration;

FIG. 27 is a perspective view of inner components of the gun shown in FIG. 1 in the fifth configuration;

FIGS. 28 and 29 are longitudinal sectional views of the gun shown in FIG. 1, in a sixth configuration;

FIG. 30 is a perspective view of inner components of the gun shown in FIG. 1 in the sixth configuration;

FIGS. 31 and 32 are longitudinal sectional views of the gun shown in FIG. 1, in a seventh configuration;

FIG. 33 is a perspective view of inner components of the gun shown in FIG. 1 in the seventh configuration;

FIGS. 34 and 35 are longitudinal sectional views of the gun shown in FIG. 1, in an eighth configuration;

FIG. 36 is a perspective view of inner components of the gun shown in FIG. 1 in the eighth configuration;

FIGS. 37 and 38 are longitudinal sectional views of the gun shown in FIG. 1, in a ninth configuration;

FIG. 39 is a perspective view of inner components of the gun shown in FIG. 1 in the ninth configuration;

FIGS. 40 and 41 are longitudinal sectional views of the gun shown in FIG. 1, in a ninth configuration;

FIG. 42 is a perspective view of inner components of the gun shown in FIG. 1 in the eighth configuration;

DETAILED DESCRIPTION OF THE INVENTION

Figure 1:
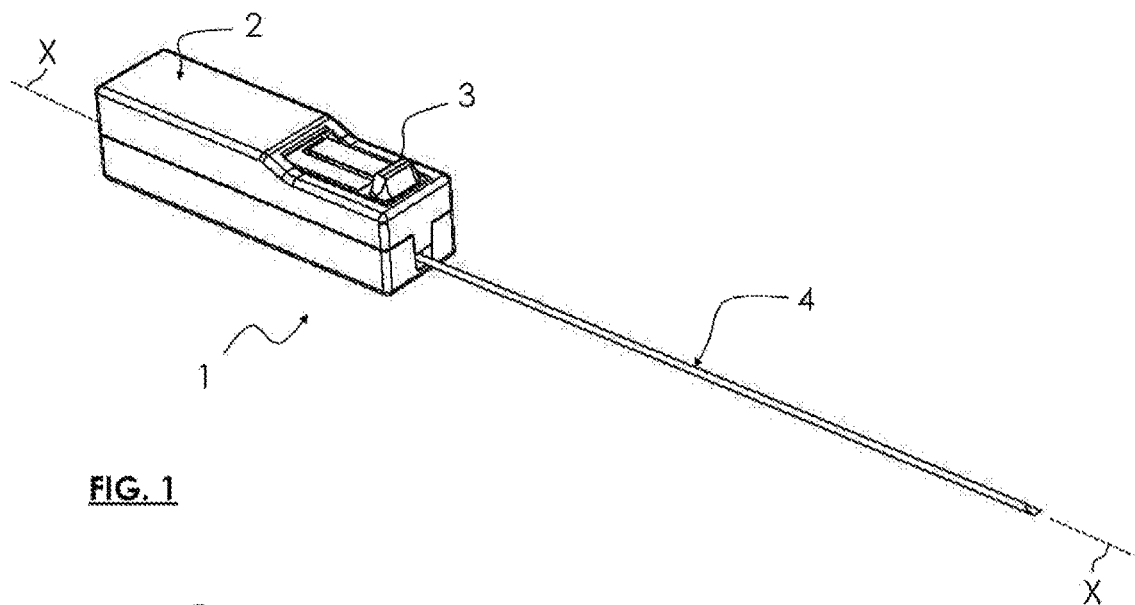
FIG. 1 is a perspective view of an automatic biopsy gun according to the present invention.

FIG. 1 is a perspective view of an automatic biopsy gun 1 according to the present invention, provided with a box-shaped body 2, a loading stud 3 and a needle 4 intended to be inserted in a patient's body in order to take a tissue sample.

It should be noted that the gun 1 is different with respect to the known art because it has a single loading stud 3, instead of the traditional two studs (one per each carriage).

For sake of simplicity, hereinafter the geometric axis X-X of the needle 4 will be considered as the longitudinal axis/direction for all the components of the gun 1.

Figure 2:
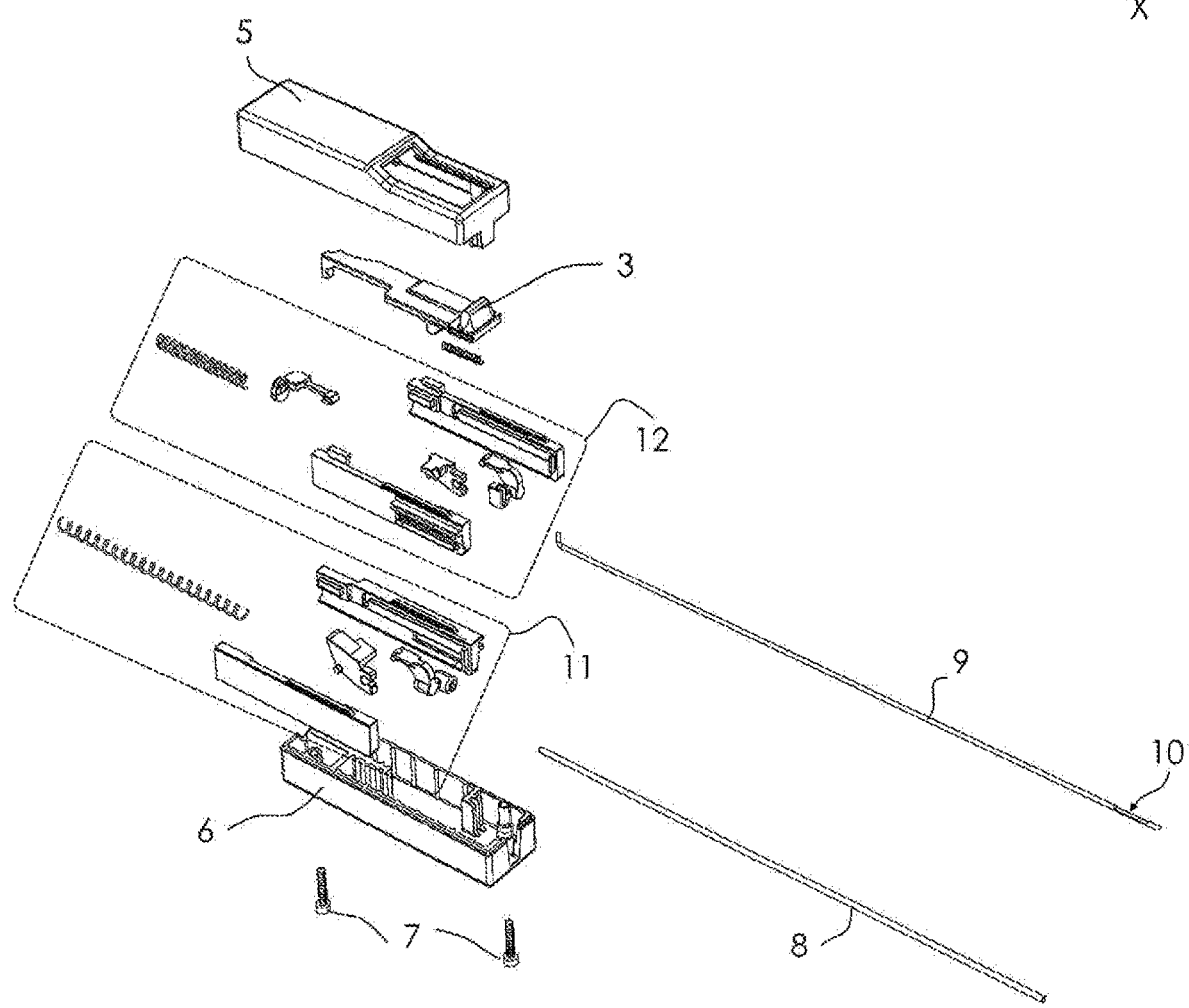
FIG. 2 is a perspective and exploded view of the gun shown in FIG. 1.

FIG. 2 shows all the components of the gun 1. As it can be seen, the box-shaped body 2 is defined by an upper body portion 5 and a lower body portion 6 that can be coupled by means of screws 7. The needle comprises two elements: a cannula 8 which remains visible from the outside, and a stylet 9 slidingly housed in the cannula 8, so as to be coaxial therewith. At the free end of the stylet 10 a collecting hollow 10 having the function of holding the tissue sample taken each time from the patient's body, is provided.

The gun 1 is provided with a first carriage assembly 11 and a second carriage assembly 12, both housed in the box-shaped body 2. As described below, an end of the cannula 8 is constrained to a component of the first carriage assembly 11 and an end of the stylet 9 is constrained to a component of the second carriage assembly 12.

FIGS. 3 to 6 show the assembling sequence of the first carriage assembly 11. The reference numeral 13 denotes a first pushing member, in turn defined by a first fastening member 14 and a corresponding first slider 15. The cannula 8 can be fixed to the fastening member 14 so as to integrally move therewith. Preferably, the coupling is reversible so as to allow the replacement of the cannula 8. The first slider 15 is provided with side projections 16 designed to interface with corresponding sliding guides of the first carriage assembly 11, as described hereinbelow. The first fastening member 14 and the first slider 15 are hinged at numeral 17 so as to rotate with respect to one another on the axis Y-Y shown in FIG. 4.

FIG. 6 is a perspective view of the first carriage assembly 11 completely assembled. The casing 18, formed by two coupled shells 19 and 20, can be seen. In FIG. 5, the right shell 20 is not yet assembled and therefore can be seen inside the first carriage assembly 11. As can be seen, in the shell 19 there is a sliding guide 22 for the first slider 15. Although not visible, an identical guide is obtained at the inner wall of the shell 20.

The guides 22 extend parallel to the longitudinal axis X-X, except the respective ends 22', which bend downwards by 90° looking at the figures.

When the first carriage assembly 11 is assembled, the side projections 16 of the first slider 15 are forced to move in the sliding guides 22 and to follow the path thereof. The corners 22' form the stops. In practice, the guides 22 are inner guides and the slider 15 represents a follower able to translate back and forth along the corresponding guide 22, as denoted by the double arrow in FIG. 6.

A spring 21 can be inserted in the box-shaped body 2 of the gun 1 for applying a pushing force to the pushing member 13 and, as a result, to the cannula 8 coupled thereto.

In more details, the shells 19 and 20 define a seat 23 for the spring 21 inside the casing 18. The seat 23 extends parallel to the longitudinal axis X-X and accommodates the compressed spring 23, so that the spring 23 can not undergo warps, i.e. it can not bend laterally thereby loosing effectiveness.

FIGS. 7 to 10 show the assembling sequence of the second carriage assembly 12. The reference numeral 24 denotes a second pushing member, in turn defined by a second fastening member 25 and a corresponding second slider 26. The stylet 9 can be fixed to the fastening member 25 so as to integrally move therewith. Preferably, the coupling is reversible so as to allow the replacement of the stylet 9. The second slider 26 is provided with side projections 27 designed to interface with corresponding sliding guides of the second carriage assembly 12, as described hereinbelow. The second fastening member 25 and the second slider 26 are hinged at numeral 28 so as to rotate with respect to one another on an axis parallel to the axis Y-Y shown in FIG. 4.

FIG. 10 is a perspective view of the second carriage assembly 12 completely assembled. The casing 29, formed by two coupled shells 30 and 31, can be seen. In FIG. 9, the right shell 31 is not yet assembled and therefore can be seen inside the second carriage assembly 12. As can be seen, in the shell 30 there is a sliding guide 32 for the second slider 26. Although not visible, an identical guide is obtained at the inner wall of the shell 31.

The guides 32 extend parallel to the longitudinal axis X-X, except the respective ends 32', which bend downwards by 90° looking at the figures.

When the second carriage assembly 12 is assembled, the side projections 27 of the second slider 26 are forced to move in the sliding guides 32, following the path thereof. In practice, the guides 32 are inner guides provided with stops 32' and the slider 26 represents a follower able to translate back and forth along the corresponding guide 32, as denoted by the double arrow in FIG. 10.

A spring 33 can be inserted in the box-shaped body 2 of the gun 1 for applying a pushing force to the pushing member 24 and therefore to the stylet 9 coupled thereto.

In more details, the shells 30 and 31 define a seat 34 for the spring 33 inside the casing 29. The seat 34 extends parallel to the longitudinal axis X-X and accommodates the compressed spring 33, so that the spring 33 can not undergo warps, i.e. it can not bend laterally thereby loosing effectiveness.

Figure 11:
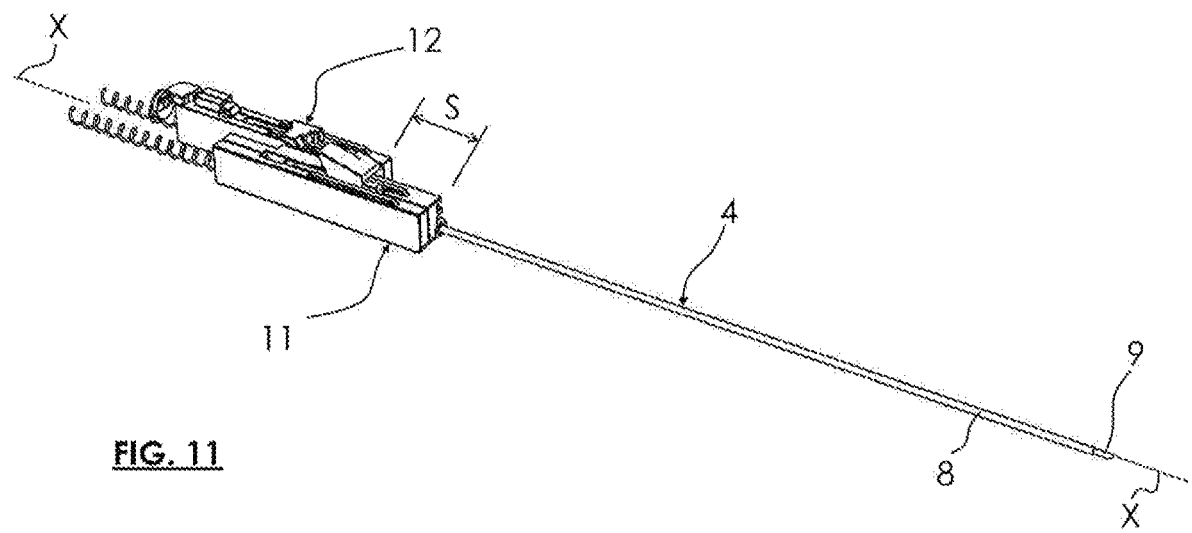
FIG. 11 is a perspective view of the first carriage and the second carriage of the gun shown in FIG. 1, constrained to each other.

FIG. 11 shows the two carriage assemblies 11 and 12 coupled to one another. Preferably they are coupled by interlocking joints. By means of this coupling, the stylet 9 can be inserted in the cannula 8; in practice, the first carriage assembly 11 and the second carriage assembly 12 must partially penetrate each other, at least by the respective fastening members 14 and 25 so that the position of the stylet 9 is coaxial with the cannula 8. For this reason, the two assemblies 11 and 12 are provided with special side windows; for example one of them can be seen in FIG. 10: through the window it is possible to see the spring 33.

It should be noted that the first carriage assembly 11 is constrained to the second carriage assembly 12 so that between the distal ends of the two assemblies, i.e. the ends facing towards the needle 4, there is a center-to-center distance S. In practice, in the box-shaped body 2 of the gun 1, the first carriage assembly 11 is located in a position on the axis X-X more advanced with respect to the second carriage assembly 12.

Figure 12:
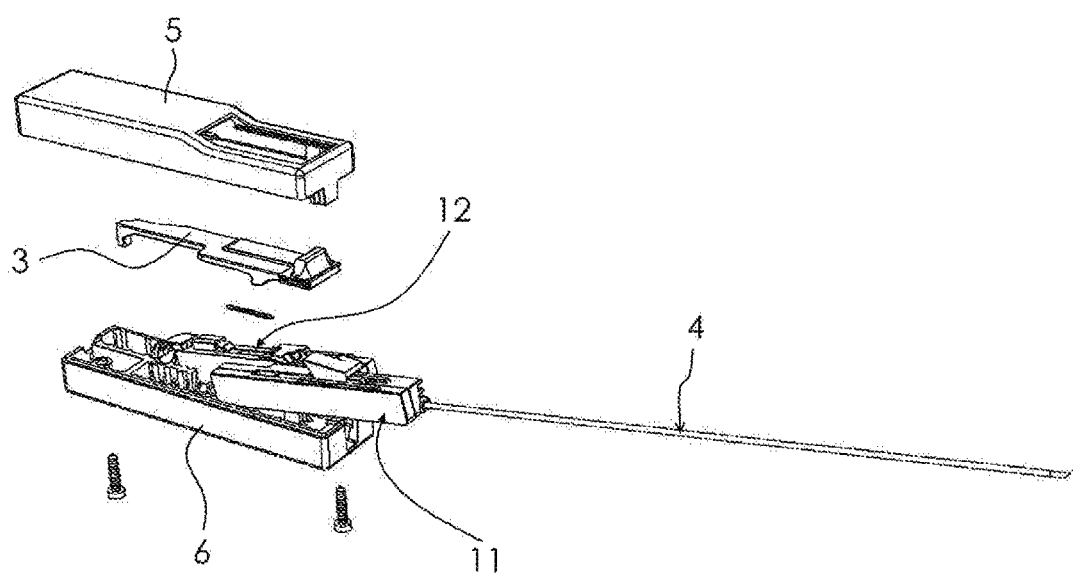
FIG. 12 is a perspective view of the gun shown in FIG. 1, in an assembling step.

FIG. 12 shows exactly the insertion of the two carriage assemblies 11 and 12 into the box-shaped body 2 of the gun 1. The longitudinal offset S between the two assemblies 11 and 12 remains unchanged.

As later described, the above described guillotine effect is actually the result of such offset S between the two assemblies 11 and 12.

The operation of the gun 1 will be now described with reference to FIGS. 13 to 42 concerning a complete loading and shooting sequence.

FIG. 13 is a sectional view of the unloaded gun 1, showing in particular the first carriage assembly 11 in the foreground.

FIG. 14 is a sectional view of the unloaded gun 1, showing in particular the second carriage assembly 12 in the foreground.

FIGS. 14 and 15 show the gun 1 in the unloaded configuration. To be able to perform a biopsy, the gun 1 must first be loaded, as explained below.

FIG. 15 shows the gun 1 without the box-shaped body 2, for greater clarity, in the same unloaded configuration shown in FIGS. 13 and 14.

As can be seen, the loading stud 3 is in its forward position, i.e. at the travel end next to the distal end of the box-shaped body 2, facing the needle 4. The springs 21 and 33 respectively of the first and second carriage assemblies 11 and 12 have the maximum possible extension inside the gun 1. Also the first pushing member 13 and the second pushing member 24 are in the most forward position.

As can be seen, the loading stud is provided at its bottom with teeth 3' and 3". The first tooth 3' is designed to mesh the first slider 15 of the first pushing member 13 during the loading step of the gun 1; the second tooth 3" is designed to mesh the second slider 26 of the second pushing member 24.

FIG. 16 is a sectional view of the gun 1 at the beginning of its loading by the healthcare professional, and particularly shows the first carriage assembly 11 in the foreground.

FIG. 17 is a sectional view of the gun 1, in the same configuration of FIG. 16 showing in particular the second carriage assembly 12 in the foreground.

FIG. 18 shows the gun 1 without the box-shaped body 2, for greater clarity, in the same configuration shown in FIGS. 16 and 17.

As can be seen, the healthcare professional partially pushed back the loading stud 3, i.e. towards the proximal end of the box-shaped body 2 thereby countering the returning action of the spring 35. The first tooth 3' engages the first slider 15 and pushes it back; in this way the entire first pushing member 13 is moved back also together with the cannula 8, which partially goes back in the box-shaped body 2. The spring 21 is partially preloaded and the tip 10 of the stylet 9 remains exposed, i.e. pulled out of the cannula 8.

As best shown in FIG. 17, in this step the second tooth 3" of the loading stud 3 does not engage with the second slider 26 of the second pushing member 24, but simply steps over it, by passing thereon.

This effect is due to the fact that the loading stud 3 is flexible and bends when it interacts with the first slider 15, or else the tooth 3" is swinging and retracts in the profile of the loading stud 3 during the passage over the second slider 26 in the loading movement. In the example shown in figures, the loading stud 3 bends just enough to allow the tooth 3" to pass over the second slider 26.

Therefore, when the healthcare professional manually pushes a first time the loading stud to the respective rearward position, only the first carriage assembly 11 is loaded, i.e. only the spring 21 is loaded and the first pushing member 13 is led to the rearward position, that is the one closest to the proximal end of the box-shaped body 2, whereas the second carriage assembly 12 remains in the initial position shown in FIGS. 13-15.

Figure 19:
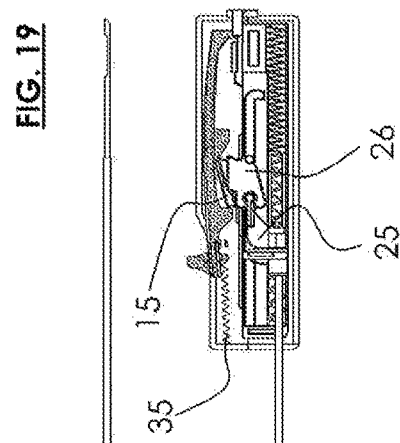
FIGS. 19 and 20 are longitudinal sectional views of the gun shown in FIG. 1, in a third configuration.

FIG. 19 is a sectional view of the gun 1 with the first carriage assembly 11 almost fully loaded, and particularly shows the first carriage assembly 11 in the foreground.

Figure 20:
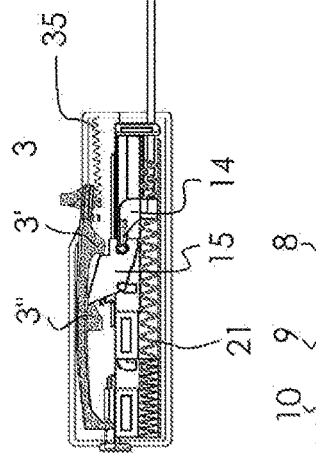

FIG. 20 is a sectional view of the gun 1, in the same configuration of FIG. 19 showing in particular the second carriage assembly 12 in the foreground.

Figure 21:
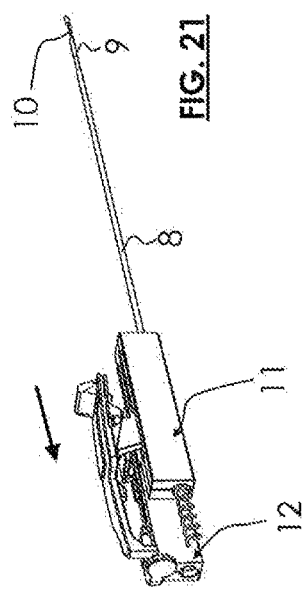
FIG. 21 is a perspective view of inner components of the gun shown in FIG. 1 in the third configuration.

FIG. 21 shows the gun 1 without the box-shaped body 2, for greater clarity, in the same configuration shown in FIGS. 19 and 20.

In FIGS. 19-21 the healthcare professional has pushed almost completely back the loading stud 3 which is thus located almost at the end of the travel towards the proximal end of the box-shaped body 2.

Figure 22:
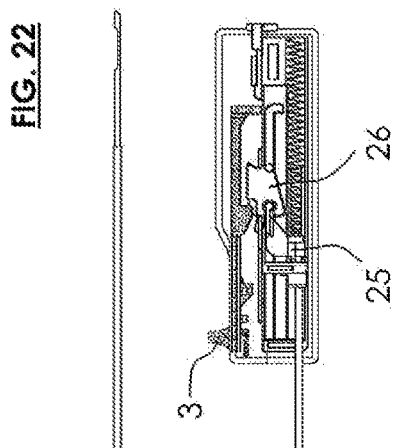
FIGS. 22 and 23 are longitudinal sectional views of the gun shown in FIG. 1, in a fourth configuration.

FIG. 22 is a sectional view of the gun 1 with the first carriage assembly 11 fully loaded and locked in position, and particularly shows the first carriage assembly 11 in the foreground.

Figure 23:
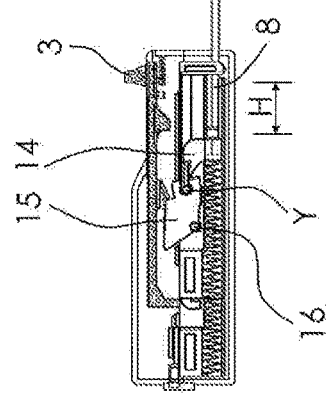

FIG. 23 is a sectional view of the gun 1, in the same configuration of FIG. 22 showing in particular the second carriage assembly 12 in the foreground.

Figure 24:
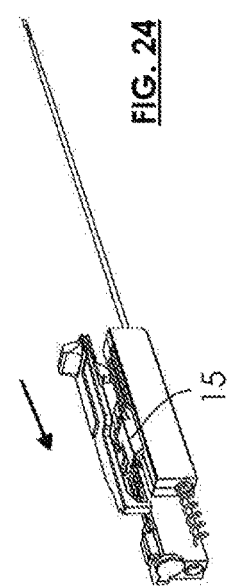
FIG. 24 is a perspective view of inner components of the gun shown in FIG. 1 in the fourth configuration.

FIG. 24 shows the gun 1 without the box-shaped body 2, for greater clarity, in the same configuration shown in FIGS. 22 and 23.

In FIGS. 22-24 the loading stud 3, after reaching the rearward position, is automatically returned to the forward position. At the rearward position of the stud 3, the first carriage assembly 11, loaded, is locked but the stud 3 is not locked therewith and is returned to the distal end of the box-shaped body 2 by the respective spring 35.

In particular, it can be noted that the first slider 15 has rotated around the Y axis with respect to the first fastening member 14. This rotation allows the first slider 15 and therefore the first pushing member 13 to be locked. The side projections 16 of the first slider 15 are forced to follow the guide 22 (see FIG. 5) obtained in the casing 18 of the first carriage assembly 11 until they engage the corners 22'.

When the side projections 16 of the first slider 15 engage the corners 22', the first slider 15 is locked although the spring 21, which is fully compressed, applies a pushing force towards the needle 4. As described below, when the shoot is triggered, the first slider 15 is lifted just enough to disengage the corners 22'.

The tooth 3' of the shooting button disengages the first slider 15 and spring 35 returns the control button 3 to its initial forward position.

As shown in FIG. 22, in the configuration with the first carriage assembly 11 loaded, the cannula 8 is partially housed in the box-shaped body 2 over a length H corresponding to the portion of the cannula 8 exposed from the tip 10 of the stylet 9.

As shown in FIG. 23, this is the time to load the second carriage assembly 12 which, in the meantime, has been stationary in the initial position.

FIG. 25 is a sectional view of the gun 1 with the first carriage assembly 11 fully loaded and locked in position, and the second carriage assembly 12 in the course of loading; in particular, FIG. 25 shows in the foreground the first group carriage 11 loaded as shown in FIG. 22 and behind it the second carriage assembly 12 in the course of loading.

FIG. 26 is a sectional view of the gun 1, in the same configuration of FIG. 25 showing in particular the second carriage assembly 12 in the foreground.

FIG. 27 shows the gun 1 without the box-shaped body 2, for greater clarity, in the same configuration shown in FIGS. 26 and 25.

In FIGS. 25-27, the healthcare professional pushes back again the loading stud 3 in order to load also the second carriage assembly 12. This time, the tooth 3" of the loading stud 3 does not step over the pushing member 24 but rather engages the latter, as best shown in FIG. 26. Hence, the healthcare professional can push also the pushing member 24 towards the respective stop to the rearward position. The side projections 27 of the second slider 26 are forced to follow the inner guide 32 obtained in the casing 29 of the second carriage assembly 12.

During the loading movement of the second carriage assembly 12, the stylet goes back in the cannula 8.

FIGS. 28-30 show exactly the moment when also the second slider 26, and therefore also the second pushing member 24, reach the stop in the rearward position, with the spring 33 fully compressed.

In other words, FIGS. 28-30 show the gun 1 fully loaded and ready to perform the biopsy; both the first and the second carriage assemblies 11 and 12 have been loaded.

In particular, FIG. 28 is a sectional view of the gun 1 with the first carriage assembly 11 fully loaded and locked in position, and the second carriage assembly 12 fully loaded and positioned; in particular FIG. 28 shows, in the foreground, the first group carriage 11 loaded as shown in FIG. 22 and, behind it, the second carriage assembly 12 also fully loaded.

FIG. 29 is a sectional view of the gun 1, in the same configuration of FIG. 28 showing in particular the second carriage assembly 12 in the foreground.

FIG. 30 shows the gun 1 without the box-shaped body 2, for greater clarity, in the same configuration shown in FIGS. 28 and 29.

When the second slider 26 reaches its stop to the rearward position, its side projections 27 (see FIG. 8) engage the corners 32' (compare FIG. 9) of the inner guides 32 obtained in the casing 29 of the second carriage assembly 12, thus remaining in a stable position therein until the healthcare professional triggers the shot. In this case, the second slider 26 rotates with respect to the second fastening member 25 at Y. At this point, the tooth 3" disengages the second slider 26 and the control button 3 is returned by the spring 35 almost completely to its initial advanced position; a short path corresponding to the shot is still to be run, as described below. The spring 33 is fully compressed.

Indeed, FIGS. 31-33 show the gun 1 at the beginning of the shooting step. For triggering the shot, the healthcare professional can use the loading stud 3 or a shooting button 36 (compare FIGS. 9 and 10) which can be positioned on the box-shaped body 2 laterally or in the back, at the proximal end.

By pressing the shooting button 36 or by leading the loading stud 3 completely forwards to the stop, thereby running the last length of its travel, the lifting of the second slider 26 of the pushing member 24 is caused. The side projections 27 of the second slider 26 are caused to come out of the corners 32' of the inner guide 32 by the lifting, so that the pushing member 24 is released and, under the action of the spring 33, suddenly moves forward towards the distal end of the box-shaped body 2.

This aspect is best shown in FIG. 32: the second slider 26—pushed by the button 36—rotates on Y with respect to the second fastening member 25 and lifts itself.

Actually, FIGS. 34-36 show the gun 1 while shooting. It is supposed that in this step the healthcare professional has inserted the needle 4 into the patient's body, at the tissue sampling point.

As can be seen in FIG. 34, in this step the first carriage assembly 11 remains stationary: the first slider 15 does not move and remains locked in the corners 22' of the respective internal guide 22. On the contrary, the second carriage assembly 12 has been activated and the second pushing member 24 is moving to the forward position guided by the inner guide 32 of the second carriage assembly 12. FIG. 35 best shows the situation. Correspondingly, the stylet 9 comes out of the cannula 8 to expose the tip and, in particular, the collecting hollow 10.

In order to automatically obtain the above described guillotine effect, at this point the cannula 8 must start to follow the stylet, slide over it and sever the tissue sample housed in the collecting hollow 10, without requiring any intervention by the healthcare professional.

FIGS. 37-39 show how this happens. In practice, when the second pushing member 24 suddenly moves forward and follows the respective guide 32, at a certain point it intercepts the first pushing member 13, by coming into abutment therewith at an appropriate tilted surface 26', and lifts the first pushing member itself thereby causing it to disengage from the corners 22' of the respective guide 22.

In FIG. 37 it can be seen precisely the first slider 15 which underwent a rotation on Y, as a result of the impact with the second slider 26, that was in motion. The first slider 15 is then lifted just enough to disengage the corners 22'; at this point the spring 21, in turn, pushes forward the first pushing member 13 together with the cannula 8.

In FIG. 38 the tilted surface 26' of the second slider 26 can be seen, which causes the first slider 15 to rotate with respect to the first fastening member 14.

FIGS. 40-42 show the final part of the shot. Both sliders 15 and 26 have been pushed by the respective springs to the forward position. The receiving compartment 10, in which there can be the tissue sample, has been returned inside the cannula 8.

The activating sequence of the two carriage assemblies 11 and 12 was properly followed and the guillotine effect was properly and automatically obtained by the healthcare professional operating a single button.

At this point, the healthcare professional extracts the needle 4 from the patient's body and, by pressing the loading stud 3, extracts the tip of the stylet 9 from the cannula 8 in order to remove the collected tissue sample. The gun 1 is now ready to be used again on the patient.

Figure 43:
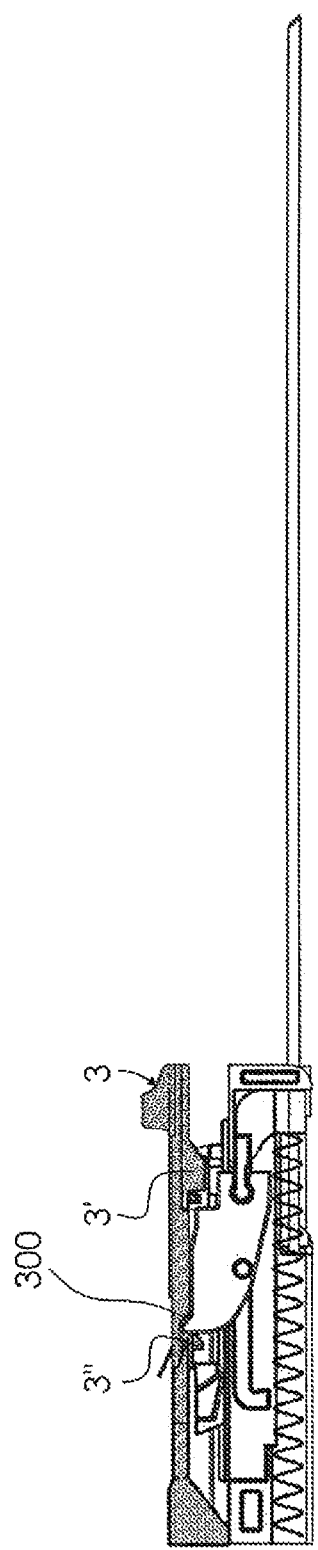
FIG. 43 is a longitudinal sectional view of a further embodiment of the gun according to the present invention, in a first configuration.

FIG. 43 shows an embodiment of the gun in which the loading stud 3 is provided with a splined profile. In particular, the stud 3 is provided at its bottom with a step 300 to prevent a long time bending of the stud 3 itself, such as shown for example in FIG. 13. In fact, this condition may cause undesired localized stiffening of the material, for example plastic, forming the stud 3. The step 300 allows this drawback to be prevented.

Figure 44:
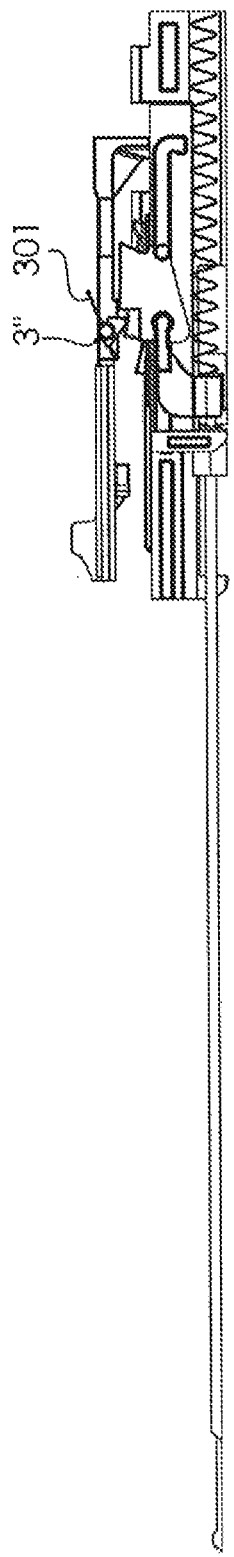
FIG. 44 is a longitudinal sectional view of the gun shown in FIG. 43.

FIG. 44 shows the same gun of FIG. 43. As it can be seen, in this case the second tooth 3" is swinging because it is pivoted exactly on the stud 3. The tooth 3" is always returned downwards, i.e. projecting from the stud 3, by a spring 301.

The invention claimed is:
1. An automatic biopsy gun (1), comprising:
a box-shaped body (2),
a needle (4) cantileverly extending from the box-shaped body (2) in a longitudinal direction (X-X), wherein the needle (4) in turn comprises a stylet (9) provided with a collecting hollow (10) to collect a tissue sample, and a cannula (8), wherein the stylet (9) is slidingly housed in the cannula (8) so that the collecting hollow (10) can emerge from the cannula (8) and return inside with a guillotine effect,
a first pushing member (13) constrained to the cannula (8) and movable in the box-shaped body (2) parallel to said longitudinal direction between a forward position, at which the cannula (8) is completely extended from the box-shaped body (2), and a rearward position, at which the cannula (8) is partially inserted in the box-shaped body (2),
a second pushing member (24) constrained to the stylet (9) and movable in the box-shaped body (2) parallel to said longitudinal direction between a forward position, at which the stylet (9) is completely extended from the box-shaped body (2), and a rearward position, at which the stylet (9) is partially inserted in the box-shaped body (2),
first and second elastic countering means (21, 33) to bias the first pushing member (13) and the second pushing member (24), and
driving means (3) to drive the first pushing member (13) and the second pushing member (24), operable by a user,
wherein the first pushing member (13) and the second pushing member (24) are guided by respective first and second inner guides (22, 32) that are inside the box-shaped body (2) and the first pushing member (13) and the second pushing member (24) are movable in their respective inner guides (22, 32) parallel to one another, side by side, and the first inner guide (22) of the first pushing member (13) and the second inner guide (32) of the second pushing member (24) are staggered along said longitudinal direction, and wherein each inner guide (22, 32) extends longitudinally and a first stop corresponding to the rearward position of the first pushing member (13) is a deviation (22') of the first inner guide (22), and a second stop corresponding to the rearward position of the second pushing member (24) is a deviation (32') of the second inner guide (32),
wherein the first pushing member (13) comprises:
a first fastening member (14) constrained to the cannula (8), and - a first slider (15) hinged to the first fastening member (14) to be rotatable with respect to the first fastening member (14) on an axis (Y-Y) orthogonal to said longitudinal direction (X-X) and provided with engaging portions (16) to engage the first inner guide (22), so that said engaging portions (16) follow a length of the first inner guide (22) and the first slider (15) acts as a follower in the first inner guide (22), or wherein the second pushing member (24) comprises:
a second fastening member (25) constrained to the stylet (9), and - a second slider (26) hinged to the second fastening member (25) rotatable with respect to the second fastening member (25) on an axis (Y-Y) orthogonal to said longitudinal direction (X- X) and provided with engaging portions (27) to engage the second inner guide (32), so that the engaging portions (27) follow a length of the second inner guide (32) and the second slider (26) acts as a follower in the second inner guide (32), and wherein said engaging portions (16, 27) are cylindrical protrusions that point contact with the respective first or second inner guide (22, 32).

2. The automatic biopsy gun (1) according to claim 1, wherein the first inner guide (22) of the first pushing member (13) and the second inner guide (32) of the second pushing member (24) have the same longitudinal extent, which allow the respective pushing members (13, 24) to run equal travels, and are longitudinally staggered of a length corresponding to a maximum possible exposure of the stylet (9) with respect to the cannula (8).

3. The automatic biopsy gun (1) according to claim 1, wherein the first and second elastic countering means (21, 33) are springs, and wherein the springs (21, 33) are extended when the respective pushing member (13, 24) is in the forward position and are compressed when the respective pushing member (13, 24) is in the rearward position.

4. The automatic biopsy gun (1) according to claim 3, wherein the springs (21, 33) are housed in appropriate seats (23, 34) that prevent deformations in directions transversal to said longitudinal direction.

5. The automatic biopsy gun (1) according to claim 1, further comprising:
a first carriage assembly (11) in turn provided with a first casing (18), and wherein the first pushing member (13) and the first elastic countering means (21) are part of the first carriage assembly (11) and the first inner guide (22) is positioned at an inner walls of the first casing (18);
a second carriage assembly (12) in turn provided with a second casing (29), and wherein the second pushing member (24) and the second elastic countering means (33) are part of the second carriage assembly (12) and the second inner guide (32) is positioned at an inner walls of the second casing (29).

6. The automatic biopsy gun (1) according to claim 1, wherein the driving means (3) consist of a loading stud (3) mounted on the box-shaped body (2) and sliding between a forward position and a rearward position, wherein the loading stud (3) comprises at least a first tooth (3') and a second tooth (3") engagable with the first pushing member (13) and the second pushing member (24), respectively.

7. The automatic biopsy gun (1) according to claim 6, wherein the loading stud (3) is a single stud configured to load both the first pushing member (13) and the second pushing member (24) by carrying out two corresponding travels.

8. The automatic biopsy gun (1) according to claim 6, wherein the loading stud (3) is at least partially flexible for bending, so to allow the second tooth (3") to step over the second pushing member (24) when the first pushing member (13) is led to the rearward position and to allow engaging the second pushing member (24) when the second pushing member (24) is led to the rearward position, thereby allowing the first and second elastic countering means (21, 33) to be loaded in two times.

9. The automatic biopsy gun (1) according to claim 6, wherein the loading stud (3) is configured to unlock the second pushing member (24) when in the respective rearward position, thereby triggering a shot.

10. The automatic biopsy gun (1) according to claim 1, wherein the second pushing member (24) is provided with a tilted surface (26') acting as a disengagement lever to disengage the first pushing member (13) from said first stop (22') when the second pushing member (24) is released from the rearward position to the forward position, so that the first pushing member (13) moves suddenly forward.

11. The automatic biopsy gun (1) according to claim 1, further comprising a shooting button (36) positioned on the box-shaped body (2) laterally or rearwardly towards the user, wherein the shooting button (36) is adapted to unlock the second pushing member (24) from said second stop (32') in the second guide (32) in order to allow the second elastic countering means (33) to move the second pushing member (24) to the forward position.

12. An automatic biopsy gun (1), comprising:
a box-shaped body (2),
a needle (4) cantileverly extending from the box-shaped body (2) in a longitudinal direction (X-X), wherein the needle (4) in turn comprises a stylet (9) provided with a collecting hollow (10) to collect a tissue sample, and a cannula (8), wherein the stylet (9) is slidingly housed in the cannula (8) so that the collecting hollow (10) can emerge from the cannula (8) and return inside with a guillotine effect,
a first pushing member (13) constrained to the cannula (8) and movable in the box-shaped body (2) parallel to said longitudinal direction between a forward position, at which the cannula (8) is completely extended from the box-shaped body (2), and a rearward position, at which the cannula (8) is partially inserted in the box-shaped body (2),
a second pushing member (24) constrained to the stylet (9) and movable in the box-shaped body (2) parallel to said longitudinal direction between a forward position, at which the stylet (9) is completely extended from the box-shaped body (2), and a rearward position, at which the stylet (9) is partially inserted in the box-shaped body (2),
first and second elastic countering means (21, 33) to bias the first pushing member (13) and the second pushing member (24), and
driving means (3) to drive the first pushing member (13) and the second pushing member (24), operable by a user,
wherein the first pushing member (13) and the second pushing member (24) are guided by respective first and second inner guides (22, 32) that are inside the box-shaped body (2) and the first inner guide (22) of the first pushing member (13) and the second inner guide (32) of the second pushing member (24) are staggered along said longitudinal direction, wherein the first pushing member (13) comprises:
a first fastening member (14) constrained to the cannula (8), and
a first slider (15) hinged to the first fastening member (14) so that to rotate with respect to the first fastening member (14) on an axis (Y-Y) orthogonal to said longitudinal direction (X-X) and provided with first engaging portions (16) to engage the first inner guide (22), so that said first engaging portions (16) follow the length of the first inner guide (22) and the first slider (15) acts as a follower in the first inner guide (22), and/or wherein the second pushing member (24) comprises:

a second fastening member (25) constrained to the stylet (9), and a second slider (26) hinged to the second fastening member (25) rotatable with respect to the second fastening member (25) on an axis (Y-Y) orthogonal to said longitudinal direction (X- X) and provided with second engaging portions (27) to engage the second inner guide (32), so that the second engaging portions (27) follow the length of the second inner guide (32) and the second slider (26) acts as a follower in the second inner guide (32), and wherein said engaging portions (16, 27) are cylindrical protrusions that point contact with the respective first or second inner guide (22, 32).

13. The automatic biopsy gun (1) according to claim 12, wherein a first stop is a 90° corner (22') of the first inner guide (22), and a second stop is a 90° corner (32') of the second inner guide (32), and when said first engaging portions (16) are positioned at said first stop, the first pushing member (13) is in its rearward position, and when said second engaging portions (27) are positioned at said second stop, the second pushing member (24) is in its rearward position.

14. The automatic biopsy gun (1) according to claim 13, wherein upon firing the biopsy gun, said first engaging portions (16) and said second engaging portions (27) disengage the first and second stops, thereby permitting sliding of the first pushing member (13) and the second pushing member (24) along the respective inner guides (22, 32).

* * * * *